(12) United States Patent
Gordon

(10) Patent No.: US 6,902,542 B2
(45) Date of Patent: Jun. 7, 2005

(54) IDENTIFICATION SYSTEM FOR A SURGICAL CASSETTE

(75) Inventor: Raphael Gordon, San Dimas, CA (US)

(73) Assignee: Alcon, Inc., Hunenberg (CH)

( * ) Notice: Subject to any disclaimer, the term of this patent is extended or adjusted under 35 U.S.C. 154(b) by 434 days.

(21) Appl. No.: 10/153,371

(22) Filed: May 28, 2002

(65) Prior Publication Data
US 2003/0221694 A1 Dec. 4, 2003

(51) Int. Cl.[7] .................... A61M 1/00; F04B 43/08; F04B 43/12; F04B 45/06
(52) U.S. Cl. .................... 604/35; 417/477.2
(58) Field of Search ............... 604/19, 22, 27, 604/28, 30, 32, 34, 35, 43, 45, 93.01, 118, 119, 120, 246, 247, 256, 257, 317, 319, 320, 324, 540, 542, 543, 902; 417/477.2

(56) References Cited

U.S. PATENT DOCUMENTS

| | | |
|---|---|---|
| 3,615,155 A | 10/1971 | Gelbman |
| 3,674,942 A | 7/1972 | Sugaya et al. |
| 3,861,619 A | 1/1975 | Wolff |
| 4,187,057 A | 2/1980 | Xanthopoulos |
| 4,395,258 A | 7/1983 | Wang et al. |
| 4,399,332 A | 8/1983 | Furlan et al. |
| 4,443,694 A * | 4/1984 | Sanford ............... 235/462.04 |
| 4,444,548 A | 4/1984 | Andersen et al. |
| 4,475,904 A | 10/1984 | Wang |
| 4,479,761 A | 10/1984 | Bilstad et al. |
| 4,493,695 A | 1/1985 | Cook |
| 4,526,515 A | 7/1985 | DeVries |
| 4,537,561 A | 8/1985 | Xanthopoulos |
| 4,550,247 A | 10/1985 | Winter et al. |
| 4,626,248 A | 12/1986 | Scheller |
| 4,627,833 A | 12/1986 | Cook |
| 4,712,907 A | 12/1987 | Weinberger et al. |
| 4,713,051 A | 12/1987 | Steppe et al. |
| 4,735,610 A | 4/1988 | Akkas et al. |
| 4,758,220 A | 7/1988 | Sundblom et al. |
| 4,758,238 A | 7/1988 | Sundblom et al. |
| 4,773,897 A | 9/1988 | Scheller et al. |
| 4,790,816 A | 12/1988 | Sundblom et al. |
| 4,798,580 A | 1/1989 | DeMeo et al. |
| 4,810,242 A | 3/1989 | Sundblom et al. |
| 4,838,865 A | 6/1989 | Flank et al. |
| 4,878,896 A | 11/1989 | Garrison et al. |
| 4,963,131 A | 10/1990 | Wortrich |
| 5,041,096 A | 8/1991 | Beuchat et al. |
| 5,106,366 A | 4/1992 | Steppe |
| 5,163,900 A | 11/1992 | Wortrich |
| 5,246,422 A | 9/1993 | Favre |
| 5,267,956 A | 12/1993 | Beuchat |
| 5,364,342 A | 11/1994 | Beuchat et al. |
| 5,403,277 A | 4/1995 | Dodge et al. |

(Continued)

FOREIGN PATENT DOCUMENTS

| | | |
|---|---|---|
| EP | 0 320 168 B1 | 7/1993 |
| WO | WO 95/28190 | 10/1995 |

Primary Examiner—Nicholas D. Lucchesi
Assistant Examiner—Mark K. Han
(74) Attorney, Agent, or Firm—Jeffrey S. Schira

(57) ABSTRACT

A surgical system and cassette, the cassette having a series of identifying tabs that are variably opaque to translucent. By varying the opaqueness of the tabs, the surgical system can readily identify the type of cassette being used.

2 Claims, 3 Drawing Sheets

U.S. PATENT DOCUMENTS

| | | |
|---|---|---|
| 5,424,040 A | 6/1995 | Bjornsson |
| 5,429,602 A | 7/1995 | Hauser |
| 5,436,418 A | 7/1995 | Tamehira |
| 5,460,490 A | 10/1995 | Carr et al. |
| 5,499,969 A | 3/1996 | Beuchat et al. |
| 5,518,378 A | 5/1996 | Neftel et al. |
| 5,588,815 A | 12/1996 | Zaleski, II |
| 5,676,530 A | 10/1997 | Nazarifar |
| 5,704,927 A | 1/1998 | Gillette et al. |
| 5,747,824 A | 5/1998 | Jung et al. |
| 5,899,674 A | 5/1999 | Jung et al. |
| 6,036,458 A | 3/2000 | Cole et al. |
| 6,059,544 A | 5/2000 | Jung et al. |
| 6,086,598 A | 7/2000 | Appelbaum et al. |

* cited by examiner

IDENTIFICATION SYSTEM FOR A SURGICAL CASSETTE

BACKGROUND OF THE INVENTION

This invention relates generally to the field of surgical cassettes and more particularly to an identification system for surgical cassettes.

The use of cassettes with surgical instruments to help manage irrigation and aspiration flows into and out of a surgical site are well-known. See, for example, U.S. Pat. Nos. 4,493,695, 4,627,833 (Cook), U.S. Pat. No. 4,395,258 (Wang, et al.), U.S. Pat. No. 4,713,051 (Steppe, et al.), U.S. Pat. No. 4,798,850 (DeMeo, et al.), U.S. Pat. Nos. 4,758,238, 4,790,816 (Sundblom, et al.), U.S. Pat. Nos. 5,267,956, 5,364,342 (Beuchat), U.S. Pat. No. 6,036,458 (Cole, et al.) and U.S. Pat. No. 6,059,544 (Jung, et al.), the entire contents of which being incorporated herein by reference.

The fluidic performance of the surgical instrument is substantially affected by the fluidic performance of the cassette. As a result, current surgical instrumentation and cassettes are designed to work as an integral system, with the fluidic performance of the cassette designed to optimize the fluidic performance of the entire surgical system. Recent advances made in surgical instrumentation now allow the surgeon to manually or automatically control the operating parameters of the surgical instrumentation to a very fine degree. Specialized cassettes have been developed to allow the surgeon to capitalize on the advance control afforded my modern surgical instrumentation. The operating parameters of the surgical instrumentation, however, must be adjusted depending upon the cassette being used. One system, disclosed in U.S. Pat. No. 6,059,544 (Jung, et al.), has a cassette with a series of frangible tabs that can be used to allow the instrument to recognize the type of cassette being used. While such a system works very well, and has been commercially successful, an alternative method for identifying the cassette that is somewhat easier and less expensive to manufacture is desirable.

Accordingly, a need exists for a cassette identification system that does not require the use of frangible tabs.

BRIEF SUMMARY OF THE INVENTION

The present invention improves upon the prior art by providing a surgical system and cassette, the cassette having a series of identifying tabs that are variably opaque to translucent. By varying the opaqueness of the tabs, the surgical system can readily identify the type of cassette being used.

Accordingly, one objective of the present invention is to provide a surgical cassette that can be readily identified by the surgical instrument in which the cassette is used.

Another objective of the present invention is to provide a surgical cassette having a series of tabs that are rendered variable opaque in a selected pattern.

These and other advantages and objectives of the present invention will become apparent from the detailed description and claims that follow.

DETAILED DESCRIPTION OF THE INVENTION

Figure 1:
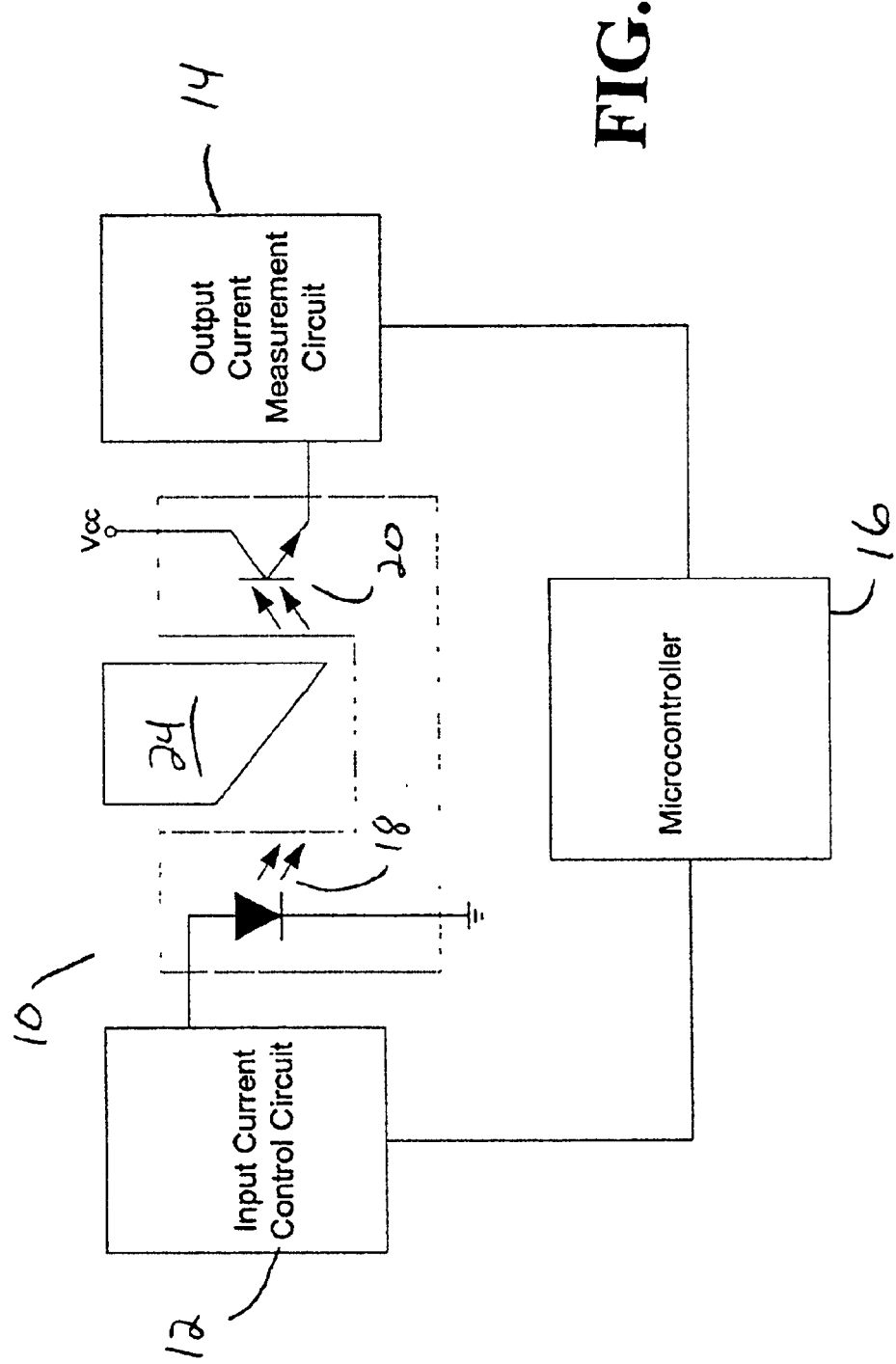
FIG. 1 is a schematic illustration of the system of the present invention.
Figure 3:
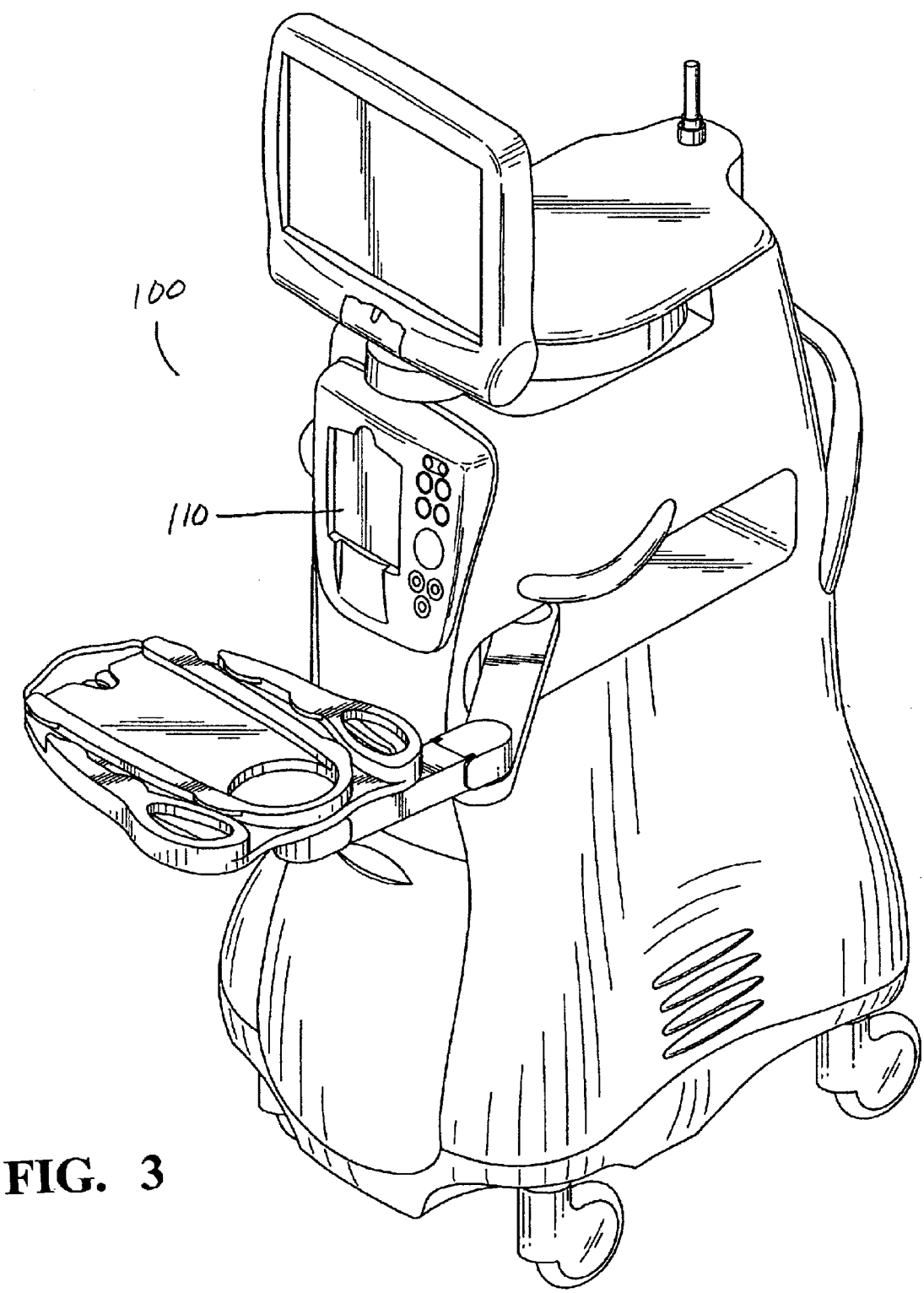
FIG. 3 is a perspective view of a surgical console that may be used with the system of the present invention.

As best seen in FIG. 1, control system 10 of the present invention generally include input current control circuit 12 and output current measurement circuit 14, both of which being connected to microcontroller 16. Input current control circuit 12 controls the input current to light emitting diodes (LEDs) 18 and output current measurement circuit 14 measures the output current from photodetectors 20. Input current control circuit 12, output current measurement circuit 14 and microcontroller 16 may be any suitable hardware and/or software system, such systems being well-known in the art. The operation of LEDs 18 and photodetectors 20 being more fully explained in U.S. Pat. No. 6,059,544 (Jung, et al.). System 10 may be included as part of the mechanical and electrical systems in any suitable surgical console, such as the console illustrated in FIG. 3.

Figure 2:
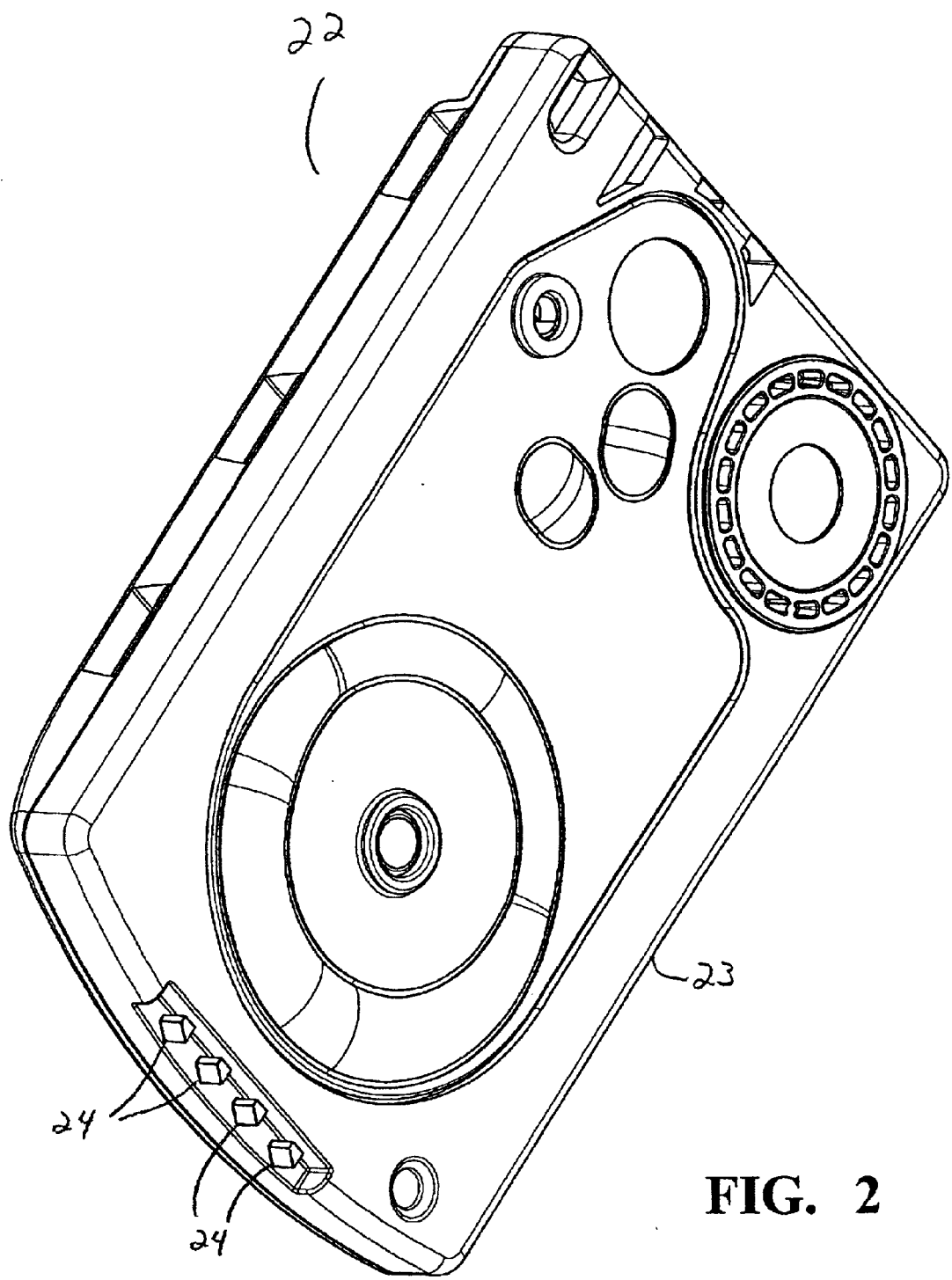
FIG. 2 is a perspective view of a cassette suitable for use with the present invention.

As best seen in FIG. 2, cassette 22 that may be used with system 10 of the present invention generally contains a plurality of tabs 24 projecting from housing 23. Tabs 24 may be generally of the shape described in U.S. Pat. No. 6,059,544 (Jung, et al.) and may be of variable opaqueness, from completely opaque to partially translucent to relatively clear. The opaqueness of tabs 24 may be used by system 10 in the manner described below. By varying the transmissibility of light through tabs 24, the number of possible distinct cassettes 22 may be increased without increasing the number of tabs 24.

In use, system 20 is calibrated by adjusting the output of LEDs 18, through input current control circuit 12, until a set output level in photodetectors 20 is achieved, as measured by output current measurement circuit 14. Upon insertion of cassette 22 into cassette receiving portion 110 of console 100, tabs 24 at least partially block the transmission of light from LEDs 18 to photodetectors 20, as shown in FIG. 1, and subsequently decrease the output of photodetectors 20. This drop in output from photodetectors 20 is sensed by output current measurement circuit 14, which relays this drop in output to microcontroller 16. Microcontroller 16 reads this decrease in the output of photodetectors 20 as an indication that cassette 22 is present in cassette receiving portion 110 of console 100. Microcontroller 16 may then instruct input current control circuit 12 to increase the output of LEDs 18 to the maximum level. Output current measurement circuit 14 then measures the output of photodetectors 20 with LEDs 18 at this maximum output level, and the output of photodetectors 20 is indirectly proportional to the opaqueness of tabs 24. In other words, the amount of light from LEDs 18 reaching photodetectors 20, and thus the output of photodetectors 20, will decrease proportionately with an increase in opaqueness of tabs 24. In this manner, the relative opaqueness of tabs 24 can be measured based on the variable amount of light reaching photodetectors 20 from LEDs 18. By varying the opaqueness of tabs 24 on cassette 24, the type of cassette 22 can be determined based on the opaqueness of tabs 24 and the pattern of variably opaque tabs 24 on cassette 22. For purposes of the present invention, each LED 18 is paired with a corresponding photodetector 20, and system 10 is arranged so that individual tabs 24 correspond to a LED/photodetector pair in a manner similar to that disclosed in U.S. Pat. No. 6,059,544 (Jung, et al.).

This description is given for purposes of illustration and explanation. It will be apparent to those skilled in the relevant art that changes and modifications may be made to the invention described above without departing from its scope or spirit.

I claim:

1. A method of identifying a surgical cassette from a plurality of surgical cassettes, the method comprising the steps of:
   a) providing a surgical console having a cassette receiving portion;
   b) providing control system having a plurality of light emitting diodes and corresponding photodetectors in the cassette receiving portion of the surgical console;
   c) calibrating the control system by adjusting the output of the light emitting diodes until a predetermined output is measured by the photodetectors;
   d) inserting a cassette into the cassette receiving portion of the surgical console, the cassette having a plurality of tabs, the tabs having variable opaqueness and at least partially block the light emitted by the light emitting diodes from reaching the photodetectors;
   e) increasing the output of the light emitting diodes to a maximum;
   f) measuring a relative opaqueness of the tabs based on a relative variability of the amount of light reaching the photodetectors through the tabs from the light emitting diodes when the light emitting diodes are at the maximum output; and
   g) identifying the cassette based on the relative opaqueness of the tabs.

2. The method of claim 1 wherein the tabs are arranged in a pattern based on the opaqueness of the individual tabs.

* * * * *